United States Patent [19]

Huebsch

[11] Patent Number: 4,888,022
[45] Date of Patent: Dec. 19, 1989

[54] ENDOPROSTHESIS

[76] Inventor: Donald L. Huebsch, 3716 Prestwick Dr., Los Angeles, Calif. 90027

[21] Appl. No.: 124,983

[22] Filed: Nov. 24, 1987

Related U.S. Application Data

[63] Continuation-in-part of Ser. No. 814,690, Dec. 30, 1985.

[51] Int. Cl.$^4$ .............................................. A61F 2/32
[52] U.S. Cl. ........................................ 623/22; 623/16
[58] Field of Search ................. 128/92 R; 623/14, 16, 623/20, 22, 23

[56] References Cited

U.S. PATENT DOCUMENTS

4,399,814 8/1983 Pratt et al. ........................ 128/92 R
4,562,598 1/1986 Kranz .................................... 623/18

Primary Examiner—Richard J. Apley
Assistant Examiner—James Prizant
Attorney, Agent, or Firm—Christie, Parker & Hale

[57] ABSTRACT

An endoprosthesis is immovably anchored in a medullary canal under a constant predetermined uniformly distributed pressure. The rigid prosthesis stem is typically embraced by an elastomeric element designed for continuous pressurization into compressed resilient anchorage with the medullary canal surface. The tubular elastomeric element can be pressurized in various ways such as by a captive gas, or by a fluent material until this material takes a set, or by a combination of pressurized gas and settable fluent material. When a captive pressurized gas is used, alone or with a settable fluent material, it provides a major portion of the elastic energy anchoring the prosthesis immovably in place; and when a settable pressurizing medium is used, the elastic energy is stored in the compressed thick elastomer. The constant elastic energy fosters bone growth to augment prosthesis anchorage. Permanent anchorage is achieved virtually instantly following alignment and pressurization of the prosthesis. The expandable/compressible elastic component readily compensates for irregularity in the canal wall and requires a minimum of preliminary preparation of its surface. The bladder can have spaced apart porous-surfaced plates bonded to the outer surface of the bladder for being expanded into contact with a cavity in the cancellous bone portion of the femur to enhance bony ingrowth during use.

8 Claims, 5 Drawing Sheets

ENDOPROSTHESIS

CROSS-REFERENCE TO RELATED APPLICATION

This is a continuation-in-part of my application Ser. No. 814,690, filed Dec. 30, 1985, which is incorporated herein by reference.

FIELD OF THE INVENTION

This invention relates to endoprostheses, and more particularly to an improved technique for anchoring an endoprosthesis in the intramedullary canal.

BACKGROUND OF THE INVENTION

To provide an endoprosthesis having immediate and long term functional reliability continues to be one of the critical objectives in orthopedic research. The typically critical aspect has been the inability to provide a simple, easily-installed, trouble-free anchorage to the medullary canal and the ability to remove the prosthesis without damaging the bone. Many techniques, structures and operating principles which have been proposed heretofore are conveniently characterized as: (1) a stem impacted into the medullary canal; (2) a stem fixed mechanically in situ by screws, pins, expansion mechanisms or the like; (3) a stem fixed by cement, (4) a porous stem gradually and eventually anchored by bone growth into the stem voids; and (5) stems equipped with one or more resilient anchorage expedients.

Each of these prior proposals is subject to shortcomings and disadvantages. Illustrative embodiments of certain of these proposals are in the following U.S. Pat. Nos., viz; Fischer 3,846,846; Rostoker 3,906,550; Kahn 3,938,198; Rybicki et al 4,011,602; Rosenberg 4,013,071; Bokros 4,038,703; Pifferi 4,051,559; Berner et al 4,124,026; Grundel et al 4,167,047; Grell et al 4,177,524; Koeneman 4,292,697; Koeneman 4,314,381; and Harris 4,406,023.

Each of these methods presents problems that can lead to failure of the arthroplasty. The problems are as follows.

In devices that are impacted into the bone canal or held in place by expansion bolts or bone screws bearing against surrounding bone, the actual surface of contact between the prosthesis and the bone may be very small and areas of stress concentration will frequently occur. Clinical observations report loosening of the implant principally due to bone resorption.

Devices requiring the use of cement for anchoring are subject to problems associated with the toxicity of the cement, necrosis of the adjacent bone, incomplete filling of the desired intramedullary space, and the absence of resiliency. In addition, reports of longterm results of cemented total hip replacements with a minimum follow-up of ten years indicate that the loosing rate on the femoral side ranges between 30 to 50 percent. This technique has the disadvantage of having a service life of five to eight years because of the cement bond becoming loose and requiring a revision (replacement of the prosthesis).

Stem emplacements relying on bony ingrowth for attachment of the stem to the bone canal wall require excellent apposition of the stem. Typically, a gap of one millimeter will exceed the growth capacity of the bone. In addition, if motion prior to fixation should occur, fibrous tissue results rather than new bone growth. In a more recent "cement-less" technique for anchoring the stem of a prosthesis in the intramedullary canal, the stem is secured within the lower portion of the canal by an impact-pressed fit (initial weight-bearing) between the stem and hard bone and by a close proximity fit of the upper portion of the stem to the cancellous bone.

In constructing a stemmed implant utilizing bony ingrowth, it has been found that several requirements should be considered. In particular, the implant must have rigid, immediate fixation so that the bone can properly grow into the porous surface of the implant. If motion occurs prior to fixation, fibrous tissue will grow instead of bone. A second requirement is excellent apposition. Typically, a gap of one or two millimeters will exceed the growth capacity of the bone and will not result in bony ingrowth. Thus, widespread and accurate apposition is absolutely essential.

Prior proposals for resilient anchorings involve various expedients utilizing coil springs having portions of their convolutions in contact with the bone, or strips of resilient material mounted on a supporting prosthesis stem and providing resilient backing for rigid elements in contact with the bone cavity. All have limited contact with the bone and lack uniformly distributed equalized pressure in a controlled predetermined amount to substantially all portions of the bone cavity opposite the body of the prosthesis.

SUMMARY OF THE INVENTION

The present invention avoids the shortcomings and disadvantages of prior endoprostheses by providing a unique simplified assembly, readily and freely insertable into the medullary canal following a minimum of preparatory operations. The invention includes elastic means compressible into high pressure resilient contact with the canal surface. Toxicity and necrosis are avoided by utilizing a biocompatible elastomer in direct contact with the canal bone tissue. The elastomer automatically compensates for irregularities in the shape and size of the canal and if the inside of the canal is substantially fully contacted by elastomer as is preferred, all portions of the canal in juxtaposition to the outer surface of the elastomer are placed under uniformly distributed pressure of a desired predetermined magnitude. Expansion of the pressurized elastomer into the natural canal irregularities rigidly anchors the prosthesis against both axial and rotary movement. In an illustrative embodiment, the elastomer comprises a tubular double walled bladder loosely embracing the stem of the prosthesis and having its opposite ends secured to the stem with provision for introducing a pressurizable medium into the bladder, or additionally between the stem and its inner wall, or into both of these chambers, serves to expand the elastomer and to hold major portions thereof elastically compressed against the canal surface. These elastic pressures can be maintained indefinitely by sealing the pressurized cavity or cavities. Moreover, these predetermined high pressures are distributed uniformly and are highly effective in fostering and promoting invigorated bone growth thereby further increasing the elastic pressure and augmenting its anchorage to the prosthesis.

Various mediums may be utilized to pressurize the prosthesis including either gaseous medium, or an initially fluid medium which takes a rigid set preferably an exothermic epoxy compound and which is maintained pressurized while setting occurs, whereby the elastomer remains permanently compressed against the canal wall, or a combination of gaseous and settable mediums. When gas alone is the pressurizing medium, thinner elastomer can be employed because the pressurized gas is a highly elastic medium.

Should circumstances arise where it is desirable to remove the prosthesis, all embodiments can accommodate this purpose. If the elastomer is maintained pressurized by either a gaseous medium or by a combination of a gaseous and a settable medium, prosthesis removal is easily and quickly achieved by venting the gaseous pressurizing medium. If only a settable pressurizing medium is utilized, prosthesis removal can be aided by providing the stem with a withdrawable wedge centrally of the stem thereby permitting the remaining portions to collapse toward one another to achieve separation from the canal wall. If a friable setting medium is employed, this is readily shattered by collapse of the stem and the application of impact and shock forces to the friable material.

Accordingly, objects and features of this invention are as follows:

(1) An improved simplified endoprosthesis and method of anchoring the same in a medullary canal while maintaining it indefinitely and immovably therein;

(2) An endoprosthesis wherein the stem is embraced by an elastomer provided with a cavity chargeable with a pressurizing medium after insertion and precise positioning of the prosthesis;

(3) An endoprosthesis having a stem supporting an elastomeric ring and provided with means for compressing the ring into uniformly distributed pressurized contact with the medullary canal;

(4) A novel method of implanting a prosthesis in a medullary canal wherein the prosthesis can be freely moved and precisely aligned with contiguous skeletal components and then immovably anchored in place under predetermined uniformly distributed pressure;

(5) An endoprosthesis having a rigid stem embraced by an elastomeric member secured to its opposite end portions and adapted to be expanded against the surface of the medullary canal under uniformly distributed pressure to foster invigorated bone growth including growth into surface irregularities of the elastomeric tube;

(6) An endoprosthesis having a pressurizable cavity including an elastomeric outer wall compressed into uniformly distributed contact with a medullary canal irrespective of irregularities in the shape and size of the canal;

(7) An endoprosthesis anchored immovably in a resilient interface with the medullary canal;

(8) An installed endoprosthesis which is collapsible inwardly following axial withdrawal of a member extending longitudinally thereof;

(9) An endoprosthesis having a nontoxic, nonmetallic uniformly pressurized resilient interface with living bone tissue;

(10) An endoprosthesis having a permanent compatible resilient elastomeric interface with living bone tissue;

(11) A prosthesis utilizing a stem of noncircular cross-section embraced by elastomer held compressed against irregularities in a medullary canal by an initially fluent pressurized settable medium to anchor the prosthesis against rotary movement;

(12) A prosthesis utilizing a rigidly settable pressurizing medium retained captive within an elastomeric envelope effective as a heat barrier between bone tissue and exothermic curing heat of the settable medium;

(13) An endoprosthesis selectively anchorable immovably in place under uniformly distributed pressure by pressurized gas, or by a settable medium, or by a combination of both retained captive in separable chamber;

(14) An endoprosthesis and method utilizing a plurality of separate concentric cavities each including at least one elastomeric wall and an outer one of which cavities is initially chargeable with gas under low pressure and an inner one of which cavities is chargeable with a pressurized medium effective to hold the outermost wall resiliently compressed against a medullary canal.

A further embodiment of the invention addresses the major problem of excellent apposition and early fixation by providing an elastomeric bladder fitted about the stem of an endoprosthesis in the cancellous bone area. The bladder is clad with an array of porous-surfaced plates. The unit is loosely fitted in the intramedullary canal, and the bladder is thereafter pressurized for expanding it and the attached plates into pressure contact with the juxtaposed surface of the cancellous bone. This ensures excellent apposition and provides immediate fixation.

These and other objects will be more fully understood by referring to the following specification and the accompanying drawings.

DETAILED DESCRIPTION

Referring initially to FIGS. 1–10, there is shown a first illustrative embodiment of the invention prosthesis, designated generally 10, installed in the upper end of a femur bone 11 after the neck and head of that bone have been severed. The femur has a dense outer sheath 12 and a lining of spongy bone tissue 13. As shown, a portion of the surface of tissue 13 has been removed in accordance with customary practice to make room for the insertion of prosthesis 10.

Figures 1, 2:
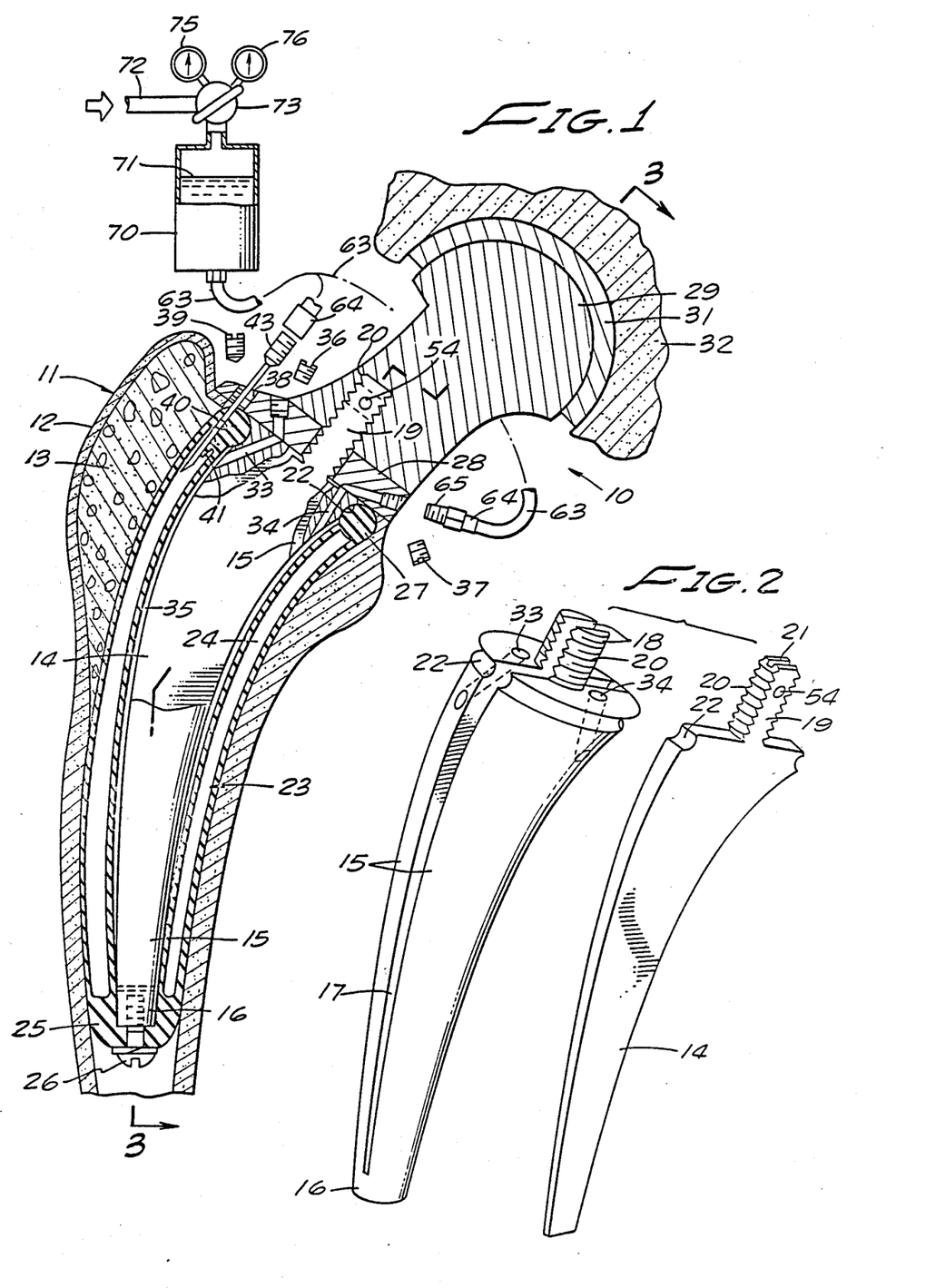
FIG. 1 is a longitudinal cross-sectional view through a first illustrative embodiment of the invention together with apparatus for charging the chambers thereof with pressurizing mediums but prior to the charging operation.
FIG. 2 is an exploded view of the stem portion of the prosthesis shown in FIG. 1.

The rigid metallic stem of the prosthesis is best shown in FIG. 2 and includes a central wedge member 14 insertable between two generally semicircular elliptical members 15, 15 interconnected at the inner smaller end 16 and separated by a slot 17 having sidewalls diverging upwardly similarly to the taper of wedge member 14. Members 14 and 15 are provided with axial extensions 18 and 19 centrally of their upper ends and each provided with threads 20 which register with one another to form a continuous spiral thread mateable with other threaded components of the assembly to be described presently. Extension 19 includes a tool seating slot 21 across its upper end. The larger outer ends of stem members 14, 15 are encircled with a groove 22 of semicircular cross-section firmly seating the inlet end of an elastomeric member to be described presently.

Stem members 14, 15 are embraced by a thick walled biocompatible elastomeric bladder 23 having an annular cavity 24, the inner wall of which cooperates with the stem elements 14, 15 in forming the cavity 35. Various elastomers which are nontoxic to live bone tissue may be used including surgical rubbers and plastics, vinyl being a particularly suitable example of many suitable elastomers. Various wall thicknesses provide excellent results, thinner walls being adequate when using a gaseous pressurizing medium and thicker walls being desirable for nongaseous and solid pressurizing charges for the cavity between the stem proper and the elastomeric wall. Wall thicknesses of $\frac{1}{8}$" to 1/16" provide excellent results.

Figures 3, 4, 5, 6:
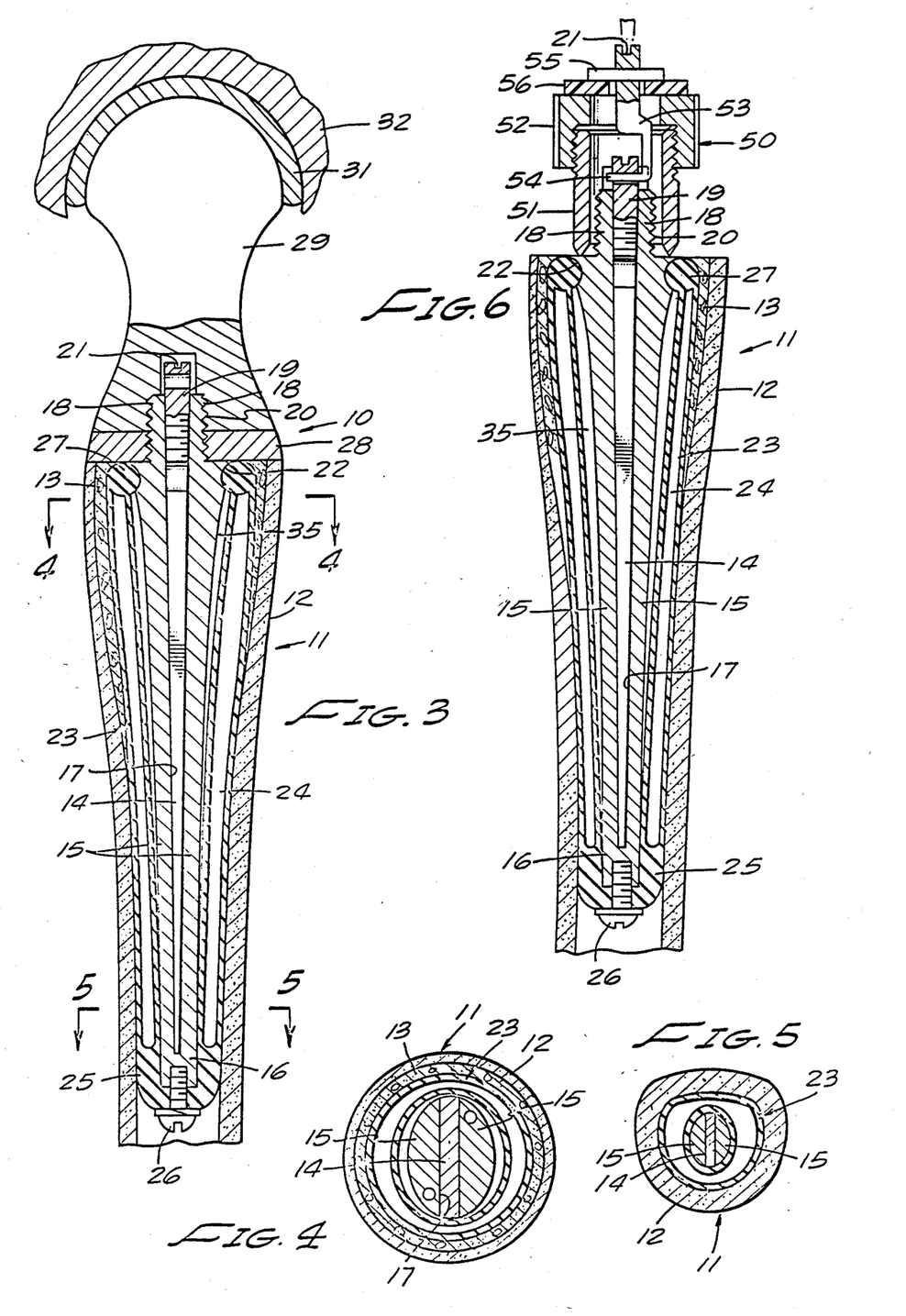
FIG. 3 is a cross-sectional view taken along the broken line 3—3 on FIG. 1.
FIG. 4 is a cross-sectional view taken along line 4—4 on FIG. 3.
FIG. 5 is a cross-sectional view taken along line 5—5 on FIG. 3.
FIG. 6 is a cross-sectional view similar to FIG. 3 but showing the head detached and the wedge puller assembled to the wedge and in readiness for use to retract the wedge.

The opposite ends of bladder 23 are secured to the adjacent end portions of the stem. As herein shown, the inner smaller end 25 is thicker and snugly embraces the lower end of stem members 15, 15 to which the elastomer is secured in a fluid tight manner by the threaded fastener 26. The outer larger end of the bladder includes a thick walled ringlet 27 having a fluid tight seat in groove 22 of the stem members. As is best shown in FIGS. 4 and 5, the assembled stem members 14 and 15 are preferably elliptically shaped with the longer axis of the ellipse lying in a plane transversely of the femur as viewed in FIG. 1. The dual purposes served by this elliptical configuration will be explained presently.

Detachably assembled to the threaded projections 18 and 19 of the stem members is a thin relatively large diameter nut 28 and a head element 29 contoured and shaped to replace the detached head and neck of the femur. Head 29 is seated in an acetabular cup 31 in the pelvis 32. Stem members 15 and nut 28 are provided with two pairs of passages 33 and 34 which are in registry with one another when nut 28 is fully tightened on the threaded projections 18 and 19. Both passages communicate with the pressurizable cavity 35 between the stem and the inner wall of the bladder 23 and their outer ends are normally closed by gasketed plugs 36, 37. One of the passages 33, 34 serves to vent cavity 35 during the charging operation and the other as a charging passage for a pressurizing medium. Nut 28 is also provided with a threaded passage 38 normally closed by a gasketed plug 39. Passage 38 is in alignment with a passage 40 through the underlying bladder ringlet 27. The inner end of passage 40 is provided with a suitable resilient, normally closed, valve such as the valve flap 41 or a conventional duck bill valve well known to persons skilled in the construction of inflatable bladders for sporting goods. Such valves open to receive a bladder charging device such as a hypodermic needle 43 and reclose automatically upon its withdrawal.

Attention is called to FIGS. 4 and 5 taken at different axial distances along the prosthesis. The medullary canal is typically naturally irregularly contoured and sized differently at different transverse locations therealong. Thus, FIG. 4 represents a typical cross-sectional view of the canal near its entrance end wherein both the bone shell and the inner surface of the canal are generally circular. In other transverse planes both the bone shell and the inner surface of the canal may and usually do vary in shape in a pronounced degree from circular. Thus, in the plane indicated in FIG. 5, both the shell and the canal wall are roughly triangular in cross-section and so oriented that the elliptically shaped stem elements 14 and 15 are disposed as indicated in FIG. 5. An important aspect of the present invention resides in the fact that despite these customary and typical irregularities, the construction and operating principles of the prosthesis bladder automatically, reliably and completely compensate for these irregularities. Moreover, the expansion of the bladder into these irregularities and into conformity with the curvate stem anchors the prosthesis immovably in place and against all rotary or longitudinal movement. Rotary movement is also safeguarded by making the stem elliptical in cross-section. These features characterizing this invention avoid the need for extensive and time consuming contouring of the canal surface and assure that substantially the entire length of the embraced portion of the prosthesis will be in predetermined uniform pressure contact with live bone tissue.

FIG. 6 shows a puller assembly 50 used to remove the prosthesis should this ever become desirable for any reason when the inner bladder cavity 35 is charged with a pressurized exothermic medium such as epoxy or plaster of Paris. Removal is accomplished by detaching the head 29. Then a screw driver is inserted in the slot 21 at the outer end of extension 19 while a second tool is employed to unscrew nut 28 from the threaded projections 18 and 19 at the outer ends of stem members 14 and 15. A puller assembly, designated generally 50, comprising the elements shown at the top of FIG. 6 are then assembled astride the projections 18 and 19. The puller includes a short bifurcated sleeve 51, a threaded bushing 52 assembled to its threaded upper end and a J-shaped puller member 53 having the hook at its lower end seated in a hole 54 extending across the upper end of the wedge member 14. A pin 55 extends through the upper end of the stem portion of puller 53 and is seated on a washer 56 resting on bushing 52. The bifurcated lower end of sleeve 51 straddles projections 18 and 19 and bears against the tops of the two stem members 15 resting against the opposite sides of wedge 14.

Figure 7:
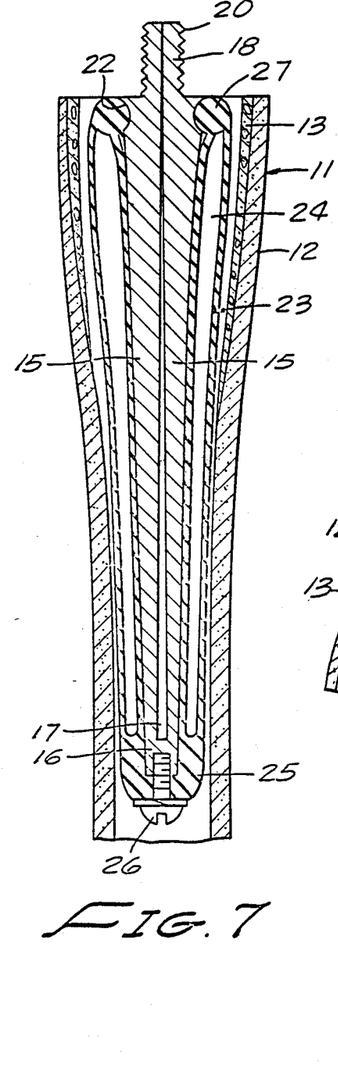
FIG. 7 is a view similar to FIG. 6 but showing the wedge detached and the remaining components of the stem collapsed together to separate the prosthesis from the medullary canal.

When bushing 52 is rotated to move upwardly along the threads of sleeve 51 it will be evident that the hook member 53 acts to withdraw the wedge. Only a relatively short lifting movement is required to release the wedge from between stem members 15, 15 along with the puller assembly 50. Thereafter, pliers or the like are applied to the threaded projections 19 forcing these members to collapse members 15, 15 inwardly against one another as shown in FIG. 7 releasing the elastic bladder 23 from the live bone tissue. The portion of the rigid epoxy or plaster of Paris material in the innermost chamber 35 of the bladder opposite the longer axis of the elliptical stem elements is relatively thin and fractures as the stem members are forcibly collapsed against one another. The elliptical shape of the stem in addition to aiding fracture of the rigid material during removal of the prosthesis also normally serves to prevent rotation within the bladder.

Figure 11:
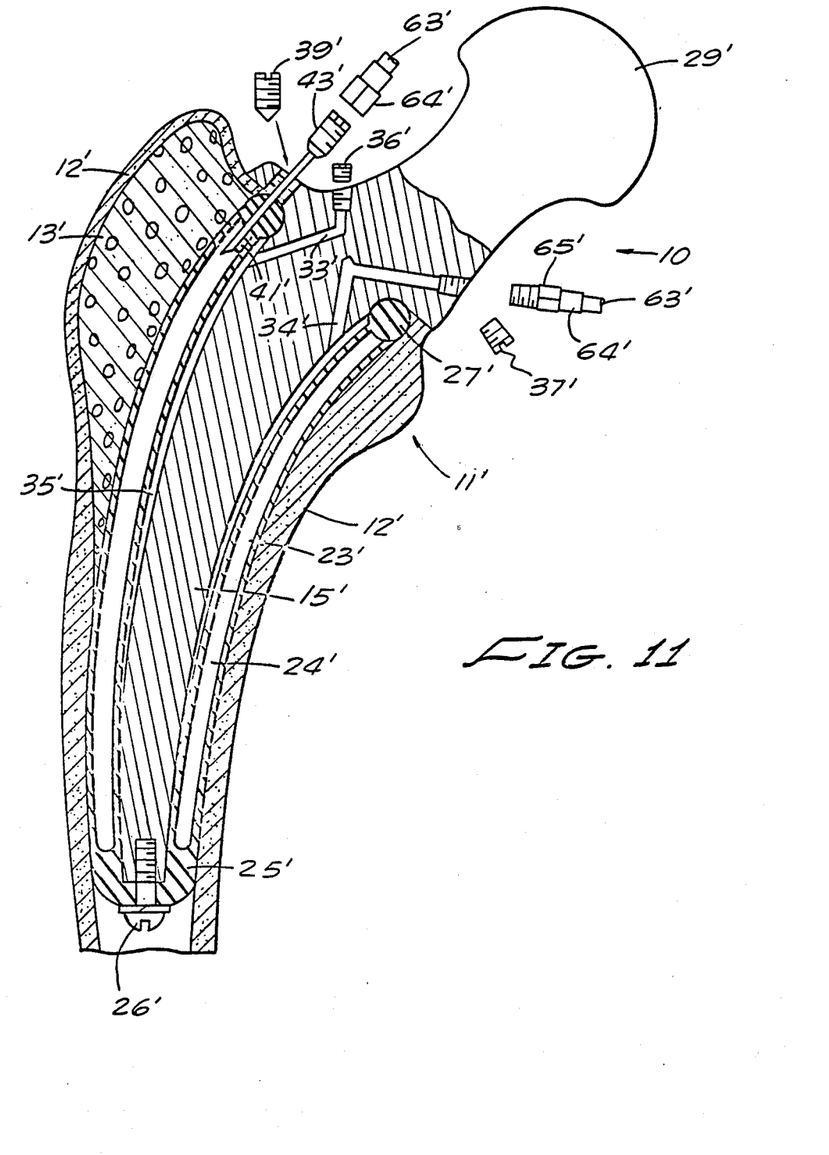
FIG. 11 is a cross-sectional view of a second preferred embodiment differing from the embodiment shown in FIGS. 11—10 in that it has a one piece stem and head.

Another illustrative embodiment of the invention is shown in FIG. 11 wherein the same or similar elements are designated by the same reference characters as in the first described embodiment but distinguished therefrom by the addition of a prime. Embodiment 10' differs structurally from the first embodiment in that it has an integral one-piece head and stem, preferably of elliptical or non-circular cross-section, made from suitable material well known to persons skilled in this art.

Both embodiments described above can be installed and pressurized in one of several modes. The head of the damaged femur is severed along a transverse plane as indicated in FIG. 1 and a portion of the spongy bone tissue 13 is removed from the medullary cavity to the extent necessary to admit the prosthesis 10, it being apparent that the elastomeric component is very flexible and inherently adapted to accommodate itself to irregularities in the cavity wall. The prosthesis bladder 23 is preferably evacuated as made or before installation and occupies a minimum of space adjacent the prosthesis stem. Accordingly, the fully assembled prosthesis is readily inserted as a unit with the base of the head lying flush against the prepared flat end of the femur.

FIG. 1 shows suitable equipment for pressurizing the interior of bladder 23 or the space 35 between the stem and the inner wall of the bladder in any selected one of the several optional pressurizing modes. This equipment comprises a container 70 chargeable with an initially fluent exothermic medium compounded to take a rigid set within a short period, such as epoxy or plaster of Paris 71. The top of this container can be pressurized with gas from a suitable source at several hundred psi via a conduit 72 connected to a flow control valve 73 having a pair of pressure gauges 75, 76. Gauge 75 indicates the pressure of the gas source and gauge 76 indicates the pressure acting on medium 71 in container 70.

The bottom of the pressurizing medium container 70 is equipped with a flexible hose 63 having a threaded fitting 64 on its outlet end. Fitting 64 can be connected either to the threaded shank of a hypodermic needle 43 or to a fitting 65 mateable with the threaded inlet of passage 34 leading into the space 35 between the prosthesis stem and the inner wall of bladder 23 depending upon whether the interior of the bladder is to be pressurized with the exothermic medium 71 or whether the space 35 between the stem and the inner wall of the bladder is to be charged with this medium. If medium 71 is not to be charged into either cavity, then container 70 is utilized empty and control valve 73 is utilized to pressurize the bladder as will be explained in detail presently.

Figure 8:
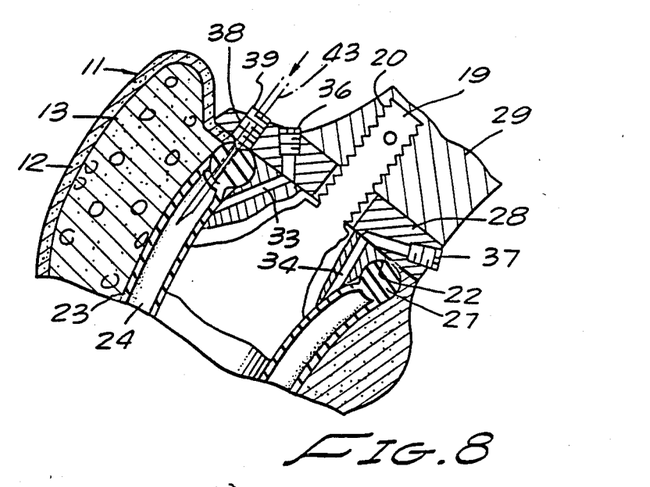
FIG. 8 is a fragmentary cross-sectional view of the upper portion of FIG. 1 showing the bladder pressurized solely by a gaseous medium.

Pressurization of the bladder of either embodiment will be described with reference to FIGS. 1 and 8. The prosthesis including its evacuated bladder is inserted into the prepared medullary cavity and is accurately aligned with the femur and the acetabular cup 31 of the bone 32. Plugs 36, 37 and 39 are removed to vent any air from between the stem and the inner wall of the bladder and to permit insertion of the hypodermic needle 43 through passage 40 in the thickened rim 27 at the upper end of the bladder thereby opening the normally closed valve 41. Coupling 64 of hose 63 is assembled to the hypodermic needle prior to the insertion of the needle into the bladder and valve 73 of the charging apparatus is thereafter manipulated to charge the bladder cavity 24 with a suitable rigidly settable material such as epoxy or plaster of Paris 71 to a desired pressure, such as 350 psi or any other superatmospheric value chosen by the surgeon as desirable. Pressures between 200 and 450 psi are suitable but a lower pressure may be selected. As previously stated, cavity 24 is evacuated eliminating the need for venting cavity 24. During the charging operation any air present in cavity 35 is vented to the atmosphere through passages 33 and 34 following which these passages are sealed closed by plugs 36, 37. Any air between the bladder outer wall and the medullary canal bone wall will be vented out between the bone and ringlet 27. When the bladder is fully charged its walls are pressed against the medullary cavity and against the prosthesis stem and maintained at the preselected pressure while the charging medium takes a rigid set. Thereafter the hypodermic needle 43 is withdrawn and plug 39 is reseated.

The thick walls of the bladder are now compressed under the preselected pressure against and in conformity with all juxtaposed areas of the medullary cavity throughout substantially the full length of the stem thereby anchoring the prosthesis immovably in place under this uniformly distributed predetermined elastic pressure.

In a second optional mode of anchoring either embodiment of the prosthesis immovably in place, the bladder cavity is charged with pressurized gas. This operation is carried out by coupling the shank of a hypodermic needle 43 to the coupling 64 of hose 63, container 70 being empty (FIG. 1). Thereafter the hypodermic needle is inserted through passage 40 at the upper end of the bladder after the closure plugs 36, 37 and 39 have been removed. Valve 73 is then opened to admit pressurized gas from source conduit 72 to a desired pressure indicated by gauge 76. Any air present in cavity 35 between the bladder and the stem is vented to the atmosphere via passages 33 and 34. The charging operation is not performed until the surgeon has taken due care to ascertain that the femur is properly aligned in the acetabular cup 31 of bone 32. When charging to a desired pressure has been attained as indicated by gauge 76, needle 43 is withdrawn as valve 41 closes automatically trapping the charged air in the bladder. Plug 39 is immediately reseated in threaded bore 38 to further seal the charge captive within the bladder. Also plugs 36 and 37 are reinstalled. The elastic pressure stored in the outer wall of the bladder is now augmented by the elastic characteristics of the pressurized gas charge in the bladder.

Figure 9:
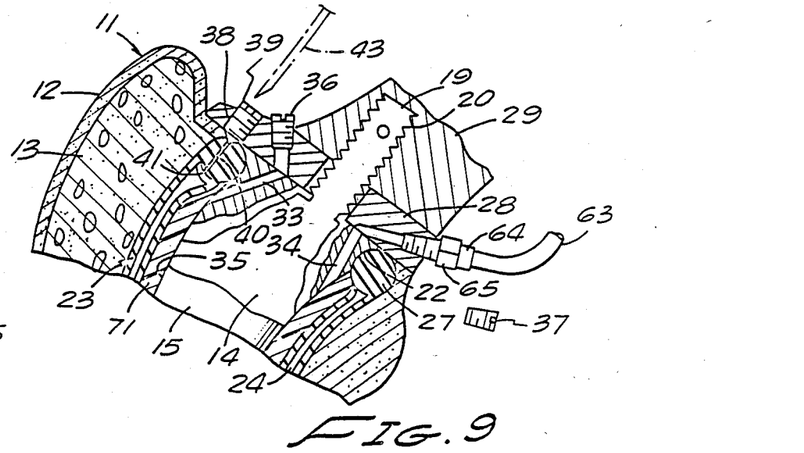
FIG. 9 is a fragmentary cross-sectional view of the upper portion of FIG. 1 showing a gas charge in the bladder and a change of a pressurized settable medium between the stem and the inner bladder wall.

Still another charging option and mode is illustrated in FIG. 9 wherein the evacuated bladder of either embodiment is inflated with gas at low pressure such as one atmosphere and is accomplished by the pressurized gas technique just described. Thereafter this trapped small quantity of gas can be pressurized to high elastic pressure by charging the exothermic medium 71 into the cavity 35 between the stem and the inner wall of bladder 23. This charging mode is carried out with the charging apparatus shown in FIG. 1 connected to the prosthesis as will now be described in connection with FIG. 9. Plugs 36, 37 are detached. Plug 39 has been reseated with low pressure gas in cavity 24. Hose 63 and its fitting 65 is connected to the inlet passage 34. The surgeon then accurately and precisely aligns the prosthesis with the femur and bone 32 and proceeds to admit pressurized epoxy or plaster of Paris from container 70 into the cavity 35 between the stem and the inner wall of bladder 23. Any air present in this cavity is vented to the atmosphere via the open passageway 33 after which plugs 36 is reseated. Pressurized epoxy is admitted under pressure by opening valve 73 until the pressure of the filled cavity reaches a desired value as indicated by pressure gauge 76. As the fluent exothermic medium 71 fills the cavity between the stem and the bladder wall, the small volume of captive gas in the bladder cavity 24 becomes pressurized to the same magnitude as the medium 71 in cavity 35. The inner and outer walls of the bladder are now nearly in contact and this small volume of highly compressed and highly elastic captive body of gas augments the high elastic compression stresses stored in the bladder walls and cooperates to hold the outer bladder wall in uniformly distributed highly elastic contact with the wall of the medullary canal. It is important that the exothermic medium be maintained pressurized for the short period of time required for it to take a rigid set. Once that has taken place, valve 73 can be closed, the hose connection 65 can be detached and plug 37 can be reseated.

Figure 10:
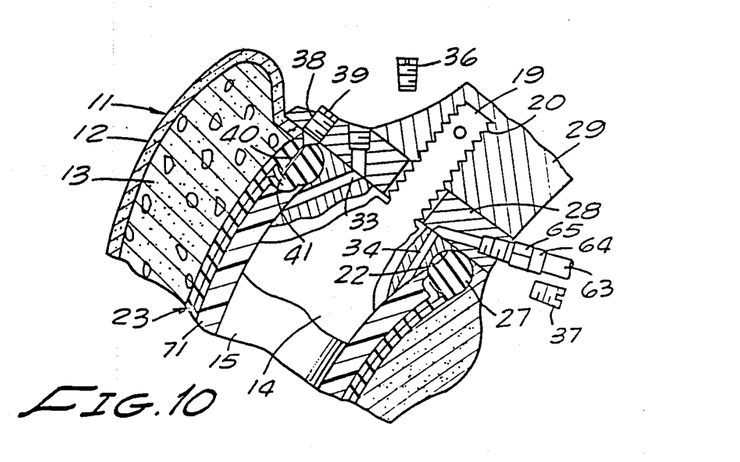
FIG. 10 is a fragmentary cross-sectional view of the upper portion of FIG. 1 showing a pressurized charge of a settable medium beween the stem and the bladder and holding both bladder walls resiliently pressed together with the outer wall pressed against the medullary canal.

Another alternate charging mode is illustrated in FIG. 10 wherein both the inner and outer walls of the evacuated bladder 23 are held elastically compressed against the medullar canal by pressurized exothermic medium 71 from container 70. The charging and installation procedure is similar to that described immediately above with minor exceptions. Both plugs 36 and 37 are detached but plug 39 remains installed and in sealing engagement with the entrance to the passage 40 for the hypodermic needle through the thick upper rim 27 of the bladder the cavity 24 having been evacuated. Fitting 65 of the flexible hose 63 is installed in the inlet of passage 34 in communication with the cavity 35 between the prosthesis stem and the inner wall of bladder 23. After accurate alignment of the prosthesis between the femur 11 and the acetabular cup of bone 32 the operator opens valve 73 of the charging apparatus to admit the exothermic medium 71 into the cavity 35 between the stem and the bladder via passage 34. Any air present in this cavity is vented to the atmosphere via passage 33. As soon as all air is released and the chamber is charged with epoxy, plug 36 is installed to seal passage 33 closed and permit a desired pressure to be applied and maintained on the medium 71 until the medium takes a rigid set to hold both walls of the bladder pressed against one another and against the wall of the bone tissue 13. Hose 63 and its fitting 65 can then be detached and the passage 34 closed by its plug 37. The combined compression energy then stored in the two walls of the bladder are available to maintain the prosthesis resiliently and immovably anchored to the femur.

Removal of either prosthesis embodiment when the bladder contains a pressurized charge of air, is facilitated by detaching plug 39 and inserting a needle 43 through passage 40 to vent the air. If the prosthesis includes a charge of an exothermic medium alone or in combination with pressurized air, removal is facilitated by use of the accessory 50 shown in FIG. 6 as will now be described.

After gaining access to the installed prosthesis, the surgeon detaches head 29 while a clamping tool is applied to nut 28 to hold the prosthesis stem stationary. A suitable tool is then inserted in slot 21 across the exposed outer end of extension 18 of the wedge component of the stem to hold the stem against rotation while nut 28 is being unwrenched. The hooked end of the J-shaped puller 53 is then installed through hole 54 in extension 19 of the wedge 14 and this is followed by inserting the bifurcated threaded sleeve 51 and bushing 52 astride extensions 18 and 19 as shown in FIG. 6 and secured to the outer end of puller member 53 by means of a washer 56 and a cross pin 55 inserted crosswise of the puller.

The bifurcated lower end of sleeve 51 straddles extensions 18 and 19 and bears against the tops of the two stem members 15 resting against the opposite sides of wedge 14. When bushing 52 is rotated to move upwardly along the threads of sleeve 51 it will be evident that the puller 53 acts to withdraw the wedge. Only a relatively short lifting movement is required to release the wedge from between stem members 15, 15 along with the puller accessory 50. Thereafter, pliers or the like are applied to the threaded extensions 19 forcing members 15, 15 to collapse inwardly against one another as shown in FIG. 7 releasing the bladder 23 from the live bone tissue. The portion of the rigid epoxy or plaster of Paris material opposite the longer axis of the elliptical stem elements is relatively thin and fractures as the stem members are forcibly collapsed against one another.

Laboratory experiments have demonstrated that bone ingrowth is stimulated when bone is subjected to load stresses beginning at about 150 psi and tapering to little or no ingrowth at 750 psi with excellent ingrowth occurring in the 250 to 350 psi range. Pressures in this range uniformly distributed over a substantial length of the bone will promote a healthy and substantial strengthening of pressurized portions of the bone by promoting bone growth toward the elastomeric member 23 to enhance the existing rigid anchorage of that member to the bone cavity. Additionally, stress levels of 150 to 350 psi between the bone and elastomeric member 23 will produce push-out stress of the stem in excess of that which the bone could normally be subjected to.

Figures 12, 13, 14:
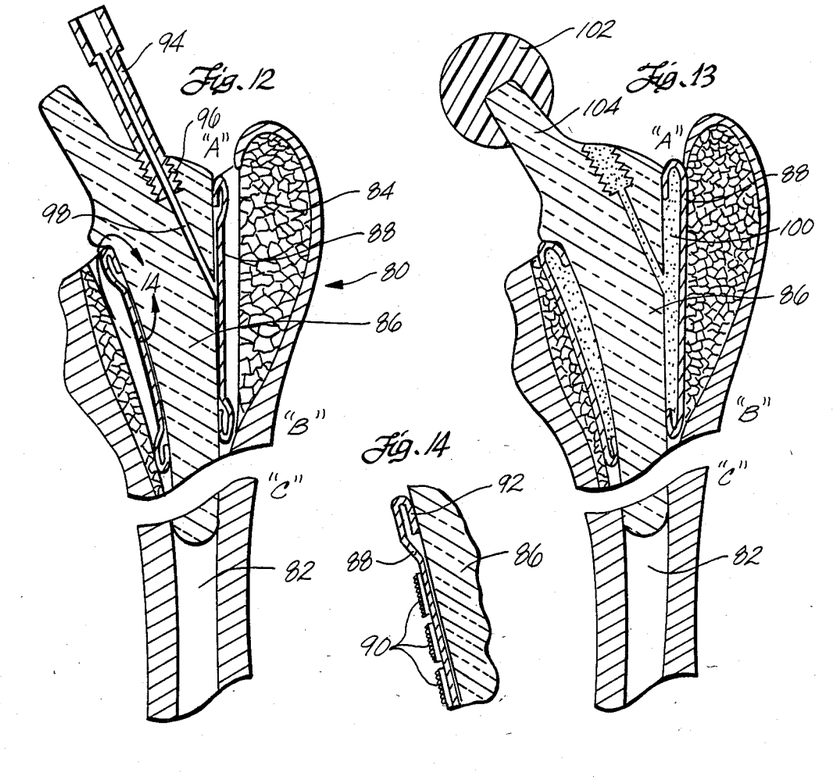
FIG. 12 is a longitudinal cross-sectional view through an alternative embodiment of the invention having and expandable bladder with porous-surfaced plates, prior to a pressurizing operation.
FIG. 13 is the same view as FIG. 12 illustrating the bladder pressurized, a pressurizing stem removed and a tapered fitted head installed in an intramedullary canal.
FIG. 14 is an enlarged view of a cross-sectional portion of the bladder of FIG. 12 illustrating the porous-surfaced plates bonded to the bladder.

FIG. 12 shows the femur 80 with the intramedullary canal 82 prepared for receiving an endoprosthesis anchored in the canal in accordance with an alternative embodiment of the invention. The canal is prepared by rasping out the cancellous bone portion 84 of the canal between "A" and "B" to a preferred tapered fit which loosely receives a bladdered portion of a rigid load bearing stem 86.

Figure 15:
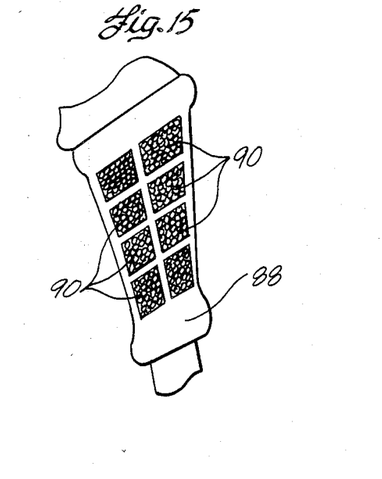
FIG. 15 is an exterior elevated view, taken on the same side as FIGS. 12 and 13, illustrating the porous-surfaced plates bonded to the bladder prior to pressurization.
Figure 16:
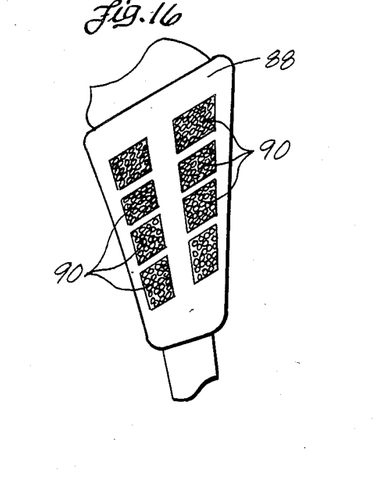
FIG. 16 is an exterior elevated view, taken on the same side as FIG. 15, illustrating the shifting of the plates, when the bladder is pressurized.

The endoprosthesis includes an expandable elastomeric bladder 88 having porous-surfaced plates 90 bonded to the outer face of the bladder. FIG. 15 shows the bladder in a normal relaxed state prior to pressurization, and FIG. 16 shows the bladder after pressurization. The bladder is preferably made from silicon rubber. The plates are mutually spaced apart around the bladder in vertically spaced apart and parallel rows. Thus, the bladders form an array in which the plates are spaced apart from each other circumferentially around the bladder and longitudinally along the length of the bladder. The plates preferably occupy a major surface portion of the bladder in the cancellous bone area of the femur. In one embodiment they occupy more than about 90% of the surface area of the bladder (in its unpressurized state) in the cancellous bone region of the femur. It is this area where the bone grows into the porous surfaces of the plates during use. The plates are preferably arranged on the bladder to occupy a major portion of its surface area in this region of the bone so as to promote bony ingrowth during use. (The plates are shown in the drawings with wider spacing between them for simplicity.) The plates are preferably thin and rectangular and are made from a rigid material such as metal. They are bonded to the surface of the bladder in its normal relaxed state. A suitable adhesive may be used for cementing the plates to the outer surface of the bladder. Preferably, the plates are bonded to a silicon rubber bladder by a bonding agent known as Chemlock 607, available from Lord Manufacturing. During expansion of the bladder as shown in FIG. 16, only those areas of the bladder between the plates expand. The cement used to bond the plates to the bladder is such that a complete bond can be achieved between the plate and the bladder without delamination during expansion of the bladder.

The plates 90 have a porous surface preferably with pore sizes between 150 and 1,000 microns. Preferably the plates are made of titanium aluminum-vanadium alloy, athough other suitable materials may be used. The porous surfaces are of a like material, or they may be formed by a ceramic material affixed to the front of the plates. The plate-clad bladder portion of the stem is preferably generally rectangular about its center in cross-section to match the contour of the medullary canal.

FIG. 14 illustrates an enlarged cross-sectional view of FIG. 12 showing the plates 90 bonded to the bladder 88. Conventional means may be used for securing the opposite ends of the bladder to the stem. As shown, the ends of the bladder are secured to the stem by a bladder flap 92 bonded to the stem, making the bladder fluid-impervious. The stem includes a removable pressurizing fitting 94 (shown in FIG. 12) threadably connected to the stem at 96. This provides means for a pressurized hardenable fluid to enter the bladder through a passage 98.

Referring to FIG. 13, the bladder is shown expanded by a hardenable fluid 100, preferably bone cement. The bladder has pressurized the plates 90 into contact with the juxtaposed surface of the cancellous bone from "A" to "B". The expanded bladder surface does not contact the bone; only the porous surfaces of the plates are held in resilient pressure contact with the bone by the bladder. This pressure contact of the porous surfaces of the plates with the cancellous bone greatly enhances the cancellous bone ingrowth into the porous plate surface during use. The stem component 86 is shown secured within the permanent pressure-fitted bladder and plate combination and with the cancellous bone between "A" and "B" and the optional pressed fit extended stem between "B" and "C". The pressurizing fitting 94 has been removed and a tapered fitted joint load bearing head 102 is installed on a neck 104 of the stem.

While particular endoprostheses methods herein shown and disclosed in detail are fully capable of attaining objects and providing advantages hereinbefore stated, it is to be understood that they are merely illustrative of the presently preferred embodiment of the invention and that no limitations are intended to the detail of construction or design herein shown other than as defined in the appended claims.

I claim:

1. An endoprosthesis freely insertable into a medullary canal and thereafter immovably anchorable thereto comprising:

an elongated load bearing stem;

elastic means mounted on and extending lengthwise of said stem; and means for compressing said elastic means radially outward into pressurized contact with the juxtaposed surface of a medullary canal, after insertion therein, under continuously maintained elastic pressure effective to secure said endoprosthesis immovably therein, said elastic means comprising an elastomeric bladder having spaced-apart porous-surfaced plates secured to its outer surface for pressure contact with the medullary canal sufficient to promote bony ingrowth into the plates in contact with said juxtaposed surface of the canal.

2. Apparatus according to claim 1 in which the bladder has an internal cavity, and including means for introducing a fluent medium under pressure to expand the bladder and maintain the plates thereon compressed in resilient contact with the medullary canal.

3. Apparatus according to claim 1 in which the porous-surfaced plates are arranged in an array around and along the outer surface of the bladder.

4. Apparatus according to claim 3 in which the porous-surfaced plates are made of metal and are adhesively bonded to the outer face of the elastomeric bladder.

5. A pressurizable elastic endoprosthesis anchoring apparatus freely insertable into a medullary canal and thereafter immovably anchorable thereto comprising:

an elongated load bearing stem;

an elastic member mounted around and extending lengthwise of said stem; and means for compressing said elastic member radially outward for pressure contact with the juxtaposed surface of the medullary canal after insertion therein;

the elastic member having a plurality of porous-surfaced plates on its outer surface for contact with said surface of the medullary canal;

the elastic member being fluid-impervious and having an interal cavity, said means for compressing said elastic member including means for introducing a fluent medium under pressure into said cavity to expand said elastic member and to continuously maintain the porous-surfaced plates on said elastic member compressed in resilient pressure contact with the medullary canal surface, said elastic member being effective to distribute said pressure substantially uniformly to the surface area of the medullary canal in contact therewith, said uniformly distributed resilient pressure applied continuously by the elastic member to the medullary canal being effective to anchor said endoprosthesis immovably therein and promote bony ingrowth into the porous-surfaced plates in pressure contact with the canal surface.

6. Apparatus according to claim 5 in which said means for compressing the elastic member includes means for introducing a pressurized fluent medium between the stem and the elastic member adapted to set rigidly and for maintaining the same pressurized while said fluent medium sets in a rigid condition thereby to maintain said elastic means elastically compressed and pressurized indefinitely.

7. A method for anchoring an endoprosthesis immovably in a medullary canal comprising:
   providing an elongated rigid load bearing stem;
   surrounding the stem with an elongated elastomeric member which is fluid-impervious and has an internal cavity, and in which the elastomeric member has porous-surfaced plates spaced apart about its outer surface;
   securing opposite end portions of the elastomeric member to a respective end of the stem;
   inserting the stem and elastomeric member into the open end of a medullary canal; and
   pressurizing the elastomeric member inwardly of an outer wall thereof with a fluent material introduced under pressure into the internal cavity to expand the outer wall of the elastomeric member radially outwardly so the porous-surfaced plates thereon are in pressurized contact with a juxtaposed surface of the medullary canal, for continuously maintaining the porous-surfaced plates compressed in resilient pressure contact with the medullary canal surface, the elastomeric member being effective to distribute the elastic pressure substantially uniformly to the surface area of the medullary canal in contact with the porous-surfaced plates thereon while said uniformly distributed elastic pressure is applied continuously by the elastomeric member to the medullary canal so as to anchor the endoprosthesis immovably therein and to promote bony ingrowth during continuous uniformly-distributed elastic pressure.

8. A pressurizable elastic endoprosthesis anchoring apparatus freely inserted into a medullary canal and thereafter immovably anchorable thereto comprising:
   a rigid main body including a load bearing stem;
   tubular elastomeric means having at least one tubular outer wall surrounding the stem with opposite end portions thereof secured to the stem in a fluid-tight manner to provide at least one closed annular cavity;
   a plurality of spaced apart porous-surfaced plates secured to the outer surface of the elastomeric means; and
   means for pressurizing said annular cavity to hold the tubular outer wall thereof with the porous-surfaced plates thereon pressed into resilient continuously maintained pressurized contact with the juxtaposed surface of a medullary canal to distribute the elastic pressure substantially uniformly to the juxtaposed surface area of the medullary canal in contact therewith to anchor the endoprosthesis immovably therein under uniformly distributed elastic pressure continuously applied by the porous-surfaced plates on the outer wall of the elastomeric means.

* * * * *